United States Patent [19]
Bills et al.

[11] Patent Number: 5,686,637
[45] Date of Patent: Nov. 11, 1997

[54] ANTIFUNGAL AGENT

[75] Inventors: Gerald F. Bills, Clark; James E. Curotto, Morgan; S. Dreikorn, Scotch Plains; Robert A. Giacobbe, Lavallette; Guy H. Harris, Cranford; Suzanne Miller Mandala, Scotch Plains; Rosemary A. Thornton, Cranford; Deborah L. Zink, Manalapen, all of N.J.; Angeles Cabello Arroyo, Madrid, Spain; Fernando Pelaez Perez, Madrid, Spain; Teresa Diez Matas, Madrid, Spain; Francisca Vicente Perez, Madrid, Spain

[73] Assignee: Merck & Co., Inc., Rahway, N.J.

[21] Appl. No.: 371,171

[22] Filed: Jan. 10, 1995

[51] Int. Cl.⁶ .................................................. C07C 59/147
[52] U.S. Cl. .......................... 554/115; 514/552; 514/547; 504/313; 436/254.1; 435/254.1; 435/256.1; 435/256.2; 435/256.3; 435/256.4; 435/256.5; 435/256.6; 435/256.7; 435/134; 435/136
[58] Field of Search .................... 884/115; 514/552, 514/547; 504/313; 436/254.1; 435/254.1, 256.1–256.7, 134, 136

[56] References Cited

PUBLICATIONS

Chemical Abstract, 88:99656 1977.

Biosis Abstract, 93:496985 1993.

Biosis Abstract, 93:317188 1993.

*Primary Examiner*—José G. Dees
*Assistant Examiner*—Deborah D. Carr
*Attorney, Agent, or Firm*—Elliott Korsen; Mark R. Daniel

[57] ABSTRACT

There is disclosed a novel compound having the formula

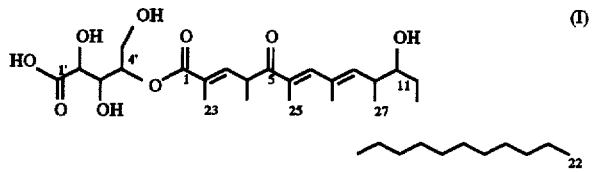

which exhibits antifungal activity.

8 Claims, No Drawings

ANTIFUNGAL AGENT

DISCLOSURE OF THE INVENTION

The present invention is directed to a compound of the formula

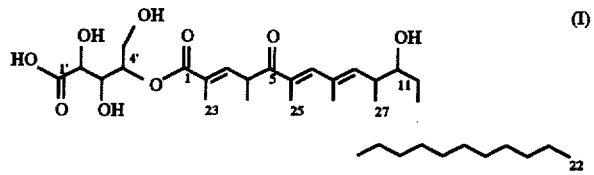

The compound has microbial and fungicidal properties and may be useful for controlling systemic and superficial fungal infections in humans with fewer side effects than standard antifungal agents such as amphotericin B or ketoconazole. Additionally, the compound exhibits utility against agricultural fungal infections.

The compound is obtained by cultivation of an unidentified fungus MF 6020.

The compound is colorless and characterized by the following spectral properties:

ULTRAVIOLET SPECTRAL DATA

λmax (CH$_3$OH): 219 nm (ε13,160), 289 nm (ε14,300)

INFRARED SPECTRAL DATA

Recorded as a thin film on ZnSe, 3428, 2924, 2854, 1712, 1661, 1614, 1453, 1373, 1246, f116, 1030 cm$^{-1}$

MASS SPECTRAL DATA

Mass spectra were recorded on Jeol SX-102A (electron impact, EI,90 eV) and JEOL HX110 (Fast Atom Bombardment, FAB) mass spectrometers. Exact mass measurements were performed at high resolution (HR-EI) using perfluorokerosene (PFK) as the internal standard. The FAB spectrum was run in a matrix of dithiothreitol dithioerythritol (20/80). The exact mass measurements were made at high resolution with ultramark 1960 (Fomblin) as the reference compound.

| HR FAB-MS | Found: | 597.3990 |
|---|---|---|
| | Calculated for C$_{33}$H$_{57}$O$_9$ (M + H): | 597.4002 |

NMR SPECTRAL DATA

NMR spectra were recorded in CD$_3$OD at 400 MHz ($^1$H) or 100 MHz ($^{13}$C). Chemical shifts are reported downfield from TMS (tetramethylsilane) and spectra were referenced to solvent peak (3.30 ppm for $^1$H spectra and 49.0 ppm for $^{13}$C spectra).

$^{13}$C NMR SPECTRA $^{13}$C: d 13.1, 13.8, 14.6, 14.8, 17.0, 18.1, 18.2, 23.8, 28.2, 30.6, 30.8, 30.86, 30.89, 31.1, 33.2, 34.7, 37.3, 37.6, 41.4, 61.5, 71.3, 71.8, 75.5, 79.8, 129.3, 133.1,134.8, 141.6, 143.8, 146.0, 168.5, 176.4, 205.0

$^1$H NMR SPECTRA $^1$H: d 0.89 (t, 7.2, 3H), 0.92 (d, 6.8, 3H), 1.00 (d, 6.8, 3H), 1.21 (d, 6.6, 3H), 1.28 (m, 18H), 1.54 (m, 2H), 1.90 (d, 1.3, 3H), 1.93 (d, 1.1, 3H), 1.95 (d, 1.3, 3H), 2.75 (m, 1H), 3.25 (dd, 5.7, 5.7, 1H), 3.82 (dd, 4.2, 12.2, 1H), 3.92 (dd, 2.8, 12.3, 1H),,4.16 (d, 1.7, 1H), 4.25 (dd, 1.9, 9.1, 1H), 4.39 (dq, 6.8, 9.8, 1H), 4.97 (ddd, 2.6, 4.2, 9.1, 1H), 5.73 (br d, 9.7, 1H), 6.78 (dq, 1.3, 9.7, 1H), 7.10 (br s, 1H)

The compound of this invention has antimicrobial properties and is especially useful as an antifungal agent against both filamentous fungi and yeasts. It is useful against organisms causing systemic human pathogenic mycotic infections such as Candida albicans, Candida sp., Candida tropicalis, Cryptococcus neofromans, Candida pseudotropicalis, Saccharomyces cerevisiae, Aspergillus flavus et al. It is also useful against organisms causing superficial fungal infections such as Trichoderma sp. and Candida sp. These properties may be effectively utilized by administering compositions containing an antifungal amount of Compound I to an area, object or subject, on or in which fungi are to be controlled. Thus, compositions containing an antifungally effective amount of Compound I and their use for the control of fungi are aspects of the present invention. An especially preferred aspect of the present invention are compositions in a pharmaceutically acceptable carrier and their use for the control of mycotic infections by administering a therapeutically effective amount of the compound.

The compound of this invention also exhibits agricultural antifungal properties. The compound can be used both to treat and control phytopathogens such as Ophiostoma ulmi, Cercospora beticola and Ustilago zeae. These properties may be utilized by administering compositions containing an antifungal amount of the compound to an area, object or subject, on or in which fungi are to be controlled. When the term control is used, it is intended to imply both prophylactic use and curative use of the compound.

The compound of the present invention is a natural product and produced by an unidentified sterile endophytic fungus MF 6020 in the culture collection of Merck & Co., Inc., Rahway, N.J., which has been deposited under the Budapest Treaty in the culture collection of the American Type Culture Collection on Oct. 28, 1994 at 12301 Parklawn Drive, Rockville, Md. 20852 and assigned accession number ATCC 74305.

The fungus which was isolated from surface-sterilized leaves of Tetragastris panamenis (Burseraceae) collected in the Golfito Wildlife Refuge, Puntarenas Province, Costa Rica, was grown on a variety of mycological media under different light regimes, and on cellulosic materials such as sterilized leaves and filter paper but in all cases it failed to sporulate and thus cannot be identified. In agar culture, colonies of the fungus exhibit the following morphology.

Colonies on oatmeal agar (Difco) at 25° C., 12 hr photoperiod attaining 32–34 mm in 21 days, appressed, with advancing zone submerged, even, with aerial mycelium scant to velvety, dull, obscurely zonate, at first translucent but soon white to pale gray, Pale Gull Gray (capitalized color names from Ridgway, R., Color standards and nomenclature, Washington D.C., 1912.), Light Gull Gray, with reverse dull gray, exudates absent.

Colonies on V8 juice agar (Mycology Guidebook, University of Washington Press, p. 665, medium M-29) at 25° C., 12 hr photoperiod attaining 30–31 mm in 21 days, submerged to appressed at the margin, raised towards the center, radially plicate, zonate, dull, transluscent to white to gray, Pallid Neutral Gray, Light Neutral Gray, Slate Gray, reverse pale gray to ochraceous gray, exudates absent.

Colonies on YM agar (Dffco) at 25° C., 12 hr photoperiod attaining 32–34 mm in 21 days, with margin submerged, even, raised, velvety, radially plicate, with some buckling of medium, zonate, white to pale gray, Light Neutral Gray, Gull Gray to dark gray, Slate Gray, Dark Neutra Gray to nearly black, Blackish Slate, reverse dark gray to nearly black, exdudates absent or with scant droplets of clear brown exudate. No growth at 37° C.

Hyphal cells are multinucleate when viewed by flurorescent staining with 4', 6'-diamidino-2-phenyindole (Sneh, Burpee & Ogoshi, *Identification of Rhizoctonia species*. American Phytopathological Society: St. Paul, 1991). The mycelium is composed of highly branched, simple septate, dematiaceous hyphae characteristic of many ascomycetous fungi.

The production of Compound I may be carried out by cultivating the fungus ATCC 74305 in a suitable nutrient medium under conditions described herein until a substantial amount of antifungal activity is detected in the fermentation broth, harvesting by extracting the active components from the mycelial growth with a suitable solvent, concentrating the solution containing the desired component, then subjecting the concentrated material to chromatographic separation to isolate Compound I from other metabolites also present in the cultivation medium.

Broadly, the sources of carbon include glucose, fructose, mannose, maltose, galactose, mannitol and glycerol, other sugars and sugar alcohols, starches and other carbohydrates, or carbohydrate derivatives such as dextran, cerelose, as well as complex nutrients such as oat flour, corn meal, millet, corn and the like. The exact quantity of the carbon source which is utilized in the medium will depend, in part, upon the other ingredients in the medium, but it is usually found that an amount of carbohydrate between 0.5 and 15 percent by weight of the medium is satisfactory. These carbon sources can be used individually or several such carbon sources may be combined in the same medium. Certain carbon sources are preferred as hereinafter set forth.

The sources of nitrogen include amino acids such as glycine, arginine, threonine, methionine and the like, ammonium salt, as well as complex sources such as yeast hydrolysates, yeast autolysates, yeast cells, tomato paste, soybean meal, casein hydrolysates, yeast extract, corn steep liquors, distillers solubles, cottonseed meal, meat extract, and the like. The various sources of nitrogen can be used alone or in combination in amounts ranging from 0.05 to 5 percent by weight of the medium.

Among the nutrient inorganic salts, which can be incorporated in the culture media are the customary saks capable of yielding sodium, potassium, magnesium, calcium, phosphate, sulfate, chloride, carbonate, and like ions. Also included are trace metals such as cobalt, manganese, iron, molybdenum, zinc, cadmium, and the like.

Representative suitable solid and liquid production media may be seen in the tables which follow. Also included is a representative seed medium.

TABLE 1

| KF SEED MEDIUM | | Trace Element Mix | |
|---|---|---|---|
| | per liter | | per liter |
| Corn Steep Liquor | 5 g | $FeSO_4.7H_2O$ | 1 g |
| Tomato Paste | 40 g | $MnSO_4.4 H_2O$ | 1 g |
| Oat flour | 10 g | $CuCl_2.2 H_2O$ | 25 mg |
| Glucose | 10 g | $CaCl_2$ | 100 mg |
| Trace Element Mix | 10 ml | $H_3BO_3$ | 56 mg |
| | | $(NH_4)_6Mo_7O_{24}.4 H_2O$ | 19 mg |
| pH = 6.8 | | $ZnSO_4.7 H_2O$ | 200 mg |

TABLE 2

| PRODUCTION MEDIUM CYS80 | |
|---|---|
| Component | per liter |
| Sucrose | 80 g |
| Corn Meal (yellow) | 50 g |
| Yeast Extract | 1 g |

No pH adjustment

TABLE 3

| PRODUCTION MEDIUM STP | |
|---|---|
| Component | per liter |
| Sucrose | 75 g |
| Tomato Paste | 10 g |
| Malt Extract | 5 g |
| $(NH_4)_2SO_4$ | 1 g |
| Soy Flour | 1 g |
| $KH_2PO_4$ | 9 g | pH adjusted to 7.0 with NaOH before autoclaving

Of the foregoing media, the CYS80 medium, was found to give the best yield of Compound I. In the production of Compound I, generally, the culture is first grown in a seed medium and the culture growth then used to inoculate a production medium. The production medium may be a solid medium or a liquid medium.

In carrying out the production of Compound I, vegetative mycelia of the culture were prepared by inoculating 54 mL of KF seed medium (Table 1) in a 250 mL unbaffled Erlenmeyer flask with 2 mL of mycelia in 10% glycerol (MF6020 wt) that had been stored at −80° C. Seed cultures were incubated for 3 days at 25° C. and 50% relative humidity on a rotary shaker with a 5-cm throw at 220 rpm in a room with constant fluorescent light. Two-mL portions of the culture were then used to inoculate a second stage seed culture and further incubated for 3 days as stated above. Two-mL portions of this 3 day culture were used to inoculate 50 mL portions of liquid production media CYS80 (Table 2) or STP (Table 3) in 250 mL unbaffled Erlenmeyer flasks. The fermentation flasks were shaken at 220 rpm. All other incubation parameters remained the same as stated above. In liquid medium CYS80 maximal production of Compound I occured between days 21–28 ( 12 mg/L). At harvest, Compound I was extracted with an equal volume of methyl ethyl ketone (MEK) by shaking with the solvent at 220 rpm for 1 hour at 25° C. The samples were centrifuged for 20 minutes at 3000 rpm to obtain the MEK layer.

The MEK extract is concentrated in vacuo to an aqueous residue. The residue is diluted with with 20 % aq. methanol or other suitable solvent, adjusted to pH 2.5 and the crude product is extracted into ethyl acetate as the free acid. The ethyl acetate extract is then subjected to silica gel step gradient chromatography. The crude product is eluted with $CH_2Cl_2$:MeOH: $H_2O$:HOAc (70:30:2:1) and purified using preparative HPLC to yield the pure product.

The usefulness of Compound I as an antifungal agent especially as an antimycotic agent may be demonstrated with Compound I in a broth microdilution assay for the determination of minimum inhibitory concentration (MIC) and minimum fungicidal concentration (MFC) against fungi. In such assay against a panel of fungi selected for their resistance/susceptibility to known compounds, animal virulence, source and clinical importance, Compound I is found to be effective at concentrations comparable to an established antifungal agent, amphotericin B.

In the microbroth dilution assay, microorganisms were selected by streaking a yeast culture on Sabouraud dextrose agar (SDA) incubating for 24–48 hours at 35°–37° C., thereafter selected 3 to 5 characteristic colonies and transferring to a fresh plate and incubating under similar conditions. From the regrowth, 3 to 5 colonies were selected and suspended in. 10 milliliters of YM broth (Difco) and incubated for 4 hours at 35°–37° C. shaking at 225 rpm. The 4 hour broth cultures were adjusted optically to 86% transmission resulting in a concentration of $1-5 \times 10^6$ cfu/ml which was further diluted 1:100 in YNBD (yeast nitrogen base with 1% dextrose) to obtain a concentration of $1-5 \times 10^4$ cfu/ml for use as inocula.

The test compound, Compound I, was prepared as a stock solution of 128 µg/ml in 20% methanol and 75 µl of said solution delivered to each well in column 1 of a 96-well, U-bottomed microtiter plate. The compounds in column 1 were then serially diluted two-fold to yield concentrations from 32 µg/ml to 0.15 µg/ml.

Amphotericin, the control compound, was prepared as a stock solution of 512 µg/ml in 10% DMSO and 75 µl of said solution delivered to each well in column 1 of a 96-well, U-bottomed microtiter plate. The compounds in column 1 were then serially diluted two-fold to yield concentrations from 128 µg/ml to 0.6 µg/ml.

The plates containing the diluted compounds were then inoculated with 75 µl/well of the appropriate microorganism and incubated for 48 hours at 35°–37° C. with MIC (minimum inhibitory concentration) determinations carried out after 24 hours of incubation. Growth and sterility controls for each organism and sterility checks for the compounds also were carded out.

After recording MICs at 24 hours, the microtiter plates were shaken gently to resuspend the cells. A 1.5 µl sample was transferred from each well of the 96-well microtiter plate to a single reservoir inoculum plate containing SDA. The inoculated SDA and corresponding microtiter plates were incubated for 24 hours at 35°–37° C. For *Cryptococus neoformans*, SDA plates were inoculated at 48 hours after recording MICs and incubated 48 hours before reading the MFC. MFC is the lowest concentration of compound at which either no growth or growth of ≤4 colonies occur.

Minimum Fungicidal Concentration (MFC)
Minimum Inhibitory Concentration (MIC)
(µg/ml)

| Strain | Compound | | Control* | |
|---|---|---|---|---|
| | MIC | MFC | MIC | MFC |
| *Candida albicans* (MY 1055) | 2 | 2 | 1 | 1 |
| *C. albicans* (CA2) | 2 | 2 | 1 | 1 |
| *C. albicans* (CLY539) | 2 | 2 | 1 | 2 |
| *C. guillermondii* (MY 1019) | 4 | 16 | 1 | 2 |
| *C. parapsilosis* (MY 1010) | 2 | 2 | 1 | 1 |
| *C. pseudotropicalis* (MY 2099) | 1 | 1 | 2 | 2 |
| *C. glabrata* (MY1381) | 4 | 4 | 2 | 2 |
| *C. topicalis* (MY1012) | 1 | 0.5 | 16 | 16 |
| *C. tropicalis* (MY1124) | 2 | 2 | 2 | 2 |
| *Cryptococcus neoformans* (MY 2062) | 2 | | 1 | |
| *Saccharomyces cerevisiae* (MY 2140) | 4 | 4 | 1 | 1 |
| *S. cerevisiae* (MY 2141) | 4 | 4 | 1 | 1 |
| *Aspergillus fumigatus* (MF 4839) | >32 | | 2 | |
| *A. fumigatus* (5668) | >32 | | 2 | |

*Amphotericin B

Compound I is also useful for inhibiting the growth of filamentous fungi. Such use may be illustrated in the following tests with *Aspergillus flavus*, *Fusarium oxysporum*, *usalago zeae* and the like.

Inocula for filamentous fungi are prepared by scraping the surface of stock plates maintained on potato dextrose agar with a moistened sterile dacron swab. The spores and mycelia are then suspended in 10 milliliters of sterile potato dextrose broth and adjusted to 70 percent transmission at 660 nm.

The samples to be tested for production of antifungal agent are applied directly to the agar plates as methanol solutions. When the sample to be tested is crude broth, it may be centrifuged prior to application. The assay plates are then incubated at either 28° C. or 37° C. for 24 hours. Following incubation, the inhibition zones are measured. Growths are also noted as to appearance. Compound I is seen to effectively inhibit growth of the fungal organisms.

The following example illustrates the invention but is not to be construed as limiting the invention disclosed herein.

EXAMPLE I

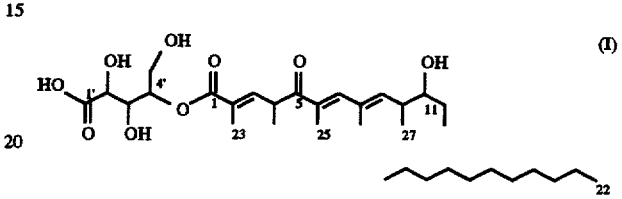

The MEK layer (1000 mL) from a 27 day fermentation in CYS80 medium was concentrated in vacuo to 58 mL. The concentrate was diluted with 342 mL H$_2$O and 100 mL CH$_3$OH and then adjusted to pH 2.4 with conc. H$_3$PO$_4$. This solution was extracted with 500 mL heptane and then 500 mL EtOAc. The EtOAc layer was washed with 200 mL H$_2$O, 200 mL brine and dried over anhydrous Na$_2$SO$_4$. The EtOAc solution was filtered and concentrated in vacuo to a syrup, 1.3 g, containing crude Compound I.

The crude Compound I above was separated on a column of silica gel 60 (E. Merck, 0.040–0.063 µm, 230–400 mesh, V$_b$=250 mL, 4.0×13.5 cm) which had been dry packed and then equilibrated with CH$_2$Cl$_2$: CH$_3$OH: HOAc (90:10:1). The crude Compound I was dissolved in 10 mL of CH$_2$Cl$_2$:CH$_3$OH: HOAc (90:10:1) and loaded onto the column. The column was then eluted with 700 mL CH$_2$Cl$_2$:CH$_3$OH: HOAc (90:10:1) collecting 100 mL fractions (Fr. 1–7). The column was then eluted with 1000 mL CH$_2$Cl$_2$:CH$_3$OH: HOAc (70:30:1) collecting 200 mL fractions (Fr. 8–12). Finally, the column was eluted with 600 mL CH$_3$OH containing 1% HOAc collecting 200 mL fractions (Fr. 13–15). Fractions 10–14 contained Compound I and were combined and concentrated in vacuo to 115 mL. This solution was diluted with approx. 250 mL H$_2$O and extracted with an equal volume of EtOAc. The EtOAc layer was washed with 150 mL H$_2$O, 100 mL brine, dried over anhydrous Na$_2$SO$_4$ and concentrated in vacuo to yield crude Compound I, 23.2 mg.

The crude Compound I above was purified by preparative reverse phase HPLC on Phenomenex Primesphere C8, 5 µ, 9.4×250 mm. A mobile phase consisting of CH$_3$CN: H$_2$O:conc. H$_3$PO$_4$ (80:20:0.1) was used at a flow rate of 4 mL / min., a column temperature of 40° C. and detection at 220 or 290 nm. Compound I eluted at 11.0 min. Fractions containing Compound I were combined, concentrated in vacuo to remove CH$_3$CN and the aqueous solution extracted with an equal volume of EtOAc. The EtOAc layer was washed with H$_2$O, brine, dried over anhydrous Na$_2$SO$_4$ and concentrated in vacuo to yield Compound I, 4.5 mg.

Compound I had the spectral properties previously described.

The following examples illustrate representative compositions containing Compound I.

EXAMPLE A 1000 compressed tablets each containing 500 milligrams of Compound I are prepared from the following formulation:

|  | Grams |
|---|---|
| Compound I | 500 |
| Starch | 750 |
| Dibasic calcium phosphate hydrous | 5000 |
| Calcium stearate | 2.5 |

The finely powdered ingredients are mixed well and granulated with 10 percent starch paste. The granulation is dried and compressed into tablets.

EXAMPLE B 1000 hard gelatin capsules, each containing 500 milligrams of Compound I are prepared from the following formulation:

| Compound | Grams |
|---|---|
| Compound I | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE C 250 milliliters of an injectible solution are prepared by conventional procedures from the following formulation:

| Dextrose | 12.5 grams |
|---|---|
| Water | 250 milliliters |
| Compound I | 400 milligrams |

The ingredients are blended and thereafter sterilized for use.

What is claimed is:

1. A compound having the formula

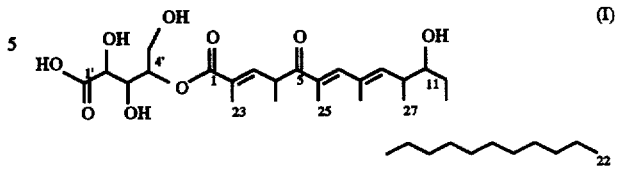

2. An antifungal composition comprising an antifungal amount of the compound of claim 1 in admixture with a biologically inert carrier.

3. A composition according to claim 2 in which the carrier is a pharmaceutically acceptable carrier.

4. A method for controlling fungal growth which comprises administering to the site where growth is to be controlled, an antifungally effective amount of a compound of claim 1.

5. A method for controlling mycotic infections in patients in need thereof which comprises administering a therapeutically effective amount of a compound of claim 1.

6. A process for producing the compound of claim 1 which comprises aerobically cultivating a culture of ATCC 74305 in a nutrient medium containing assimilable sources of carbon and nitrogen and isolating said compound therefrom.

7. A method for treating agricultural fungal infections which comprises administering to the site where growth is to be treated an effective amount of the compound of claim 1.

8. A biologically pure culture of fungus (ATCC 74305) capable of producing the compound of claim 1 in recoverable amounts.

\* \* \* \* \*